US011000249B2

(12) United States Patent
Daerr et al.

(10) Patent No.: US 11,000,249 B2
(45) Date of Patent: May 11, 2021

(54) X-RAY DETECTOR FOR GRATING-BASED PHASE-CONTRAST IMAGING

(71) Applicant: KONINKLIJKE PHILIPS N.V., Eindhoven (NL)

(72) Inventors: Heiner Daerr, Hamburg (DE); Thomas Koehler, Norderstedt (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 11 days.

(21) Appl. No.: 16/347,992

(22) PCT Filed: Nov. 9, 2017

(86) PCT No.: PCT/EP2017/078684
§ 371 (c)(1),
(2) Date: May 7, 2019

(87) PCT Pub. No.: WO2018/087195
PCT Pub. Date: May 17, 2018

(65) Prior Publication Data
US 2019/0293573 A1    Sep. 26, 2019

(30) Foreign Application Priority Data
Nov. 10, 2016   (EP) .................................... 16198076

(51) Int. Cl.
*A61B 6/00*   (2006.01)
*G01N 23/041*   (2018.01)
(Continued)

(52) U.S. Cl.
CPC .............. *A61B 6/484* (2013.01); *A61B 6/032* (2013.01); *A61B 6/035* (2013.01); *A61B 6/40* (2013.01);
(Continued)

(58) Field of Classification Search
CPC ........... A61B 6/032; A61B 6/035; A61B 6/40; A61B 6/4035; A61B 6/42; A61B 6/4208;
(Continued)

(56) References Cited

U.S. PATENT DOCUMENTS

| 4,982,096 A | * | 1/1991 | Fujii ..................... G01T 1/2018 |
| | | | 250/366 |
| 5,116,461 A | | 5/1992 | Lebby |

(Continued)

FOREIGN PATENT DOCUMENTS

| CN | 101253419 A | 8/2008 |
| EP | 1161693 | 7/2000 |
| WO | WO2010146498 A1 | 12/2010 |

OTHER PUBLICATIONS

Simon Matthias et al: "X-Ray Imaging Performance of Scintillator-filled Silicon Pore Arrays", Medical Physics, AIP, Melville, NY, US, vol. 35, No. 3, Feb. 20, 2008 (Feb. 20, 2008), pp. 968-981, XP012115967.

*Primary Examiner* — Allen C. Ho
(74) *Attorney, Agent, or Firm* — Larry Liberchuk (57) ABSTRACT

An X-ray detector (10) for a phase contrast imaging system (100) and a phase contrast imaging system (100) with such detector (10) are provided. The X-ray detector (10) comprises a scintillation device (12) and a photodetector (14) with a plurality of photosensitive pixels (15) optically coupled to the scintillation device (12), wherein the X-ray detector (10) comprises a primary axis (16) parallel to a surface normal vector of the scintillation device (12), and wherein the scintillation device (12) comprises a wafer substrate (18) having a plurality of grooves (20), which are spaced apart from each other. Each of the grooves (20) extends to a depth (22) along a first direction (21) from a first side (13) of the scintillation device (12) into the wafer substrate (18), wherein each of the grooves (20) is at least
(Continued)

partially filled with a scintillation material. Therein, the first direction (21) of at least a part of the plurality of grooves (20) is different from the primary axis (16), such that at least a part of the plurality grooves (20) is tilted with respect to the primary axis (16). An angle between the first direction (21) of a groove (20) arranged in a center region (24) of the scintillation device (12) and the primary axis (16) is smaller than an angle between the first direction (21) of a groove (20) arranged in an outer region (26) of the scintillation device (12) and the primary axis (16).

14 Claims, 3 Drawing Sheets (51) Int. Cl.
G01T 1/20 (2006.01)
G01N 23/20 (2018.01)
A61B 6/03 (2006.01)
G21K 1/02 (2006.01)

(52) U.S. Cl.
CPC .............. *A61B 6/4035* (2013.01); *A61B 6/42* (2013.01); *A61B 6/4208* (2013.01); *A61B 6/4225* (2013.01); *A61B 6/4233* (2013.01); *A61B 6/4266* (2013.01); *A61B 6/4283* (2013.01); *A61B 6/4291* (2013.01); *A61B 6/44* (2013.01); *A61B 6/4411* (2013.01); *A61B 6/4429* (2013.01); *A61B 6/4435* (2013.01); *A61B 6/4441* (2013.01); *A61B 6/4447* (2013.01); *G01N 23/041* (2018.02); *G01N 23/20075* (2013.01); *G01T 1/20* (2013.01); *G01T 1/2002* (2013.01); *G01T 1/2006* (2013.01); *G01T 1/2018* (2013.01); *G21K 1/02* (2013.01); *G21K 1/025* (2013.01); *G01N 2223/505* (2013.01); *G21K 2207/005* (2013.01)

(58) Field of Classification Search
CPC ... A61B 6/4233; A61B 6/4266; A61B 6/4283; A61B 6/4291; A61B 6/44; A61B 6/4411; A61B 6/4429; A61B 6/4435; A61B 6/4441; A61B 6/4447; A61B 6/484; G01T 1/20; G01T 1/2006; G01T 1/2018; G21K 1/02; G21K 1/025; G21K 2207/005; G01N 23/041
USPC .... 378/19, 36, 62, 98.8, 147, 149, 154, 155; 250/370.09
See application file for complete search history.

(56) References Cited

U.S. PATENT DOCUMENTS

| | | | | |
|---|---|---|---|---|
| 5,187,369 A * | 2/1993 | Kingsley | ............ | H01L 27/14663 250/367 |
| 5,812,629 A * | 9/1998 | Clauser | .................. | A61B 6/466 378/62 |
| 5,952,665 A * | 9/1999 | Bhargava | .................. | G01T 1/20 250/361 R |
| 5,956,382 A * | 9/1999 | Wiener-Avnear | ......... | G01T 1/20 250/367 |
| 6,177,236 B1 | 1/2001 | Apte | | |
| 6,452,186 B1 * | 9/2002 | Wieczorek | ............ | G01T 1/2002 250/214 VT |
| 6,744,052 B1 * | 6/2004 | Petersson | .............. | G01T 1/2018 250/361 R |
| 6,921,909 B2 * | 7/2005 | Nagarkar | ................. | G21K 4/00 250/363.01 |
| 6,987,836 B2 * | 1/2006 | Tang | ..................... | G21K 1/025 378/147 |
| 7,433,444 B2 * | 10/2008 | Baumann | ............... | A61B 6/032 378/145 |
| 7,453,981 B2 * | 11/2008 | Baumann | ............... | A61B 6/484 378/21 |
| 7,486,770 B2 * | 2/2009 | Baumann | ............... | A61B 6/032 378/145 |
| 7,492,871 B2 * | 2/2009 | Popescu | .................. | A61B 6/00 378/145 |
| 7,522,698 B2 * | 4/2009 | Popescu | ............... | A61B 6/4291 378/19 |
| 7,522,708 B2 * | 4/2009 | Heismann | ................ | A61B 6/00 378/145 |
| 7,532,704 B2 * | 5/2009 | Hempel | ................. | A61B 6/032 378/145 |
| 7,564,941 B2 * | 7/2009 | Baumann | ............... | A61B 6/484 378/146 |
| 7,639,786 B2 * | 12/2009 | Baumann | ............... | A61B 6/484 378/145 |
| 7,646,843 B2 * | 1/2010 | Popescu | .................. | A61B 6/032 378/5 |
| 7,692,156 B1 | 4/2010 | Nagarkar | | |
| 7,746,981 B2 * | 6/2010 | Takahashi | ............... | G01T 1/241 378/98.8 |
| 7,817,777 B2 * | 10/2010 | Baumann | ............... | A61B 6/4291 378/62 |
| 7,924,973 B2 * | 4/2011 | Kottler | ................. | G01N 23/041 378/36 |
| 7,945,018 B2 * | 5/2011 | Heismann | ............ | A61B 6/4233 378/62 |
| 7,949,095 B2 * | 5/2011 | Ning | ..................... | A61B 6/027 378/62 |
| 7,983,381 B2 * | 7/2011 | David | .................... | A61B 6/032 378/4 |
| 8,005,185 B2 * | 8/2011 | Popescu | .................. | A61B 6/06 378/36 |
| 8,009,796 B2 * | 8/2011 | Popescu | .................. | A61B 6/08 378/19 |
| 8,073,099 B2 * | 12/2011 | Niu | .......... | A61B 6/00 378/36 |
| 8,129,685 B2 * | 3/2012 | Nakamura | ........... | C01G 15/006 250/361 R |
| 8,165,270 B2 * | 4/2012 | David | ..................... | A61B 6/06 378/145 |
| 8,410,446 B2 * | 4/2013 | Nakamura | ........... | C01G 15/006 250/361 R |
| 8,591,108 B2 * | 11/2013 | Tada | ........................ | A61B 6/00 378/207 |
| 8,632,247 B2 * | 1/2014 | Ishii | ....................... | A61B 6/582 378/207 |
| 8,755,487 B2 * | 6/2014 | Kaneko | .................... | A61B 6/06 378/62 |
| 8,767,916 B2 * | 7/2014 | Hashimoto | ............ | A61B 6/484 378/62 |
| 8,781,069 B2 * | 7/2014 | Murakoshi | ............. | A61B 6/502 378/62 |
| 8,824,629 B2 * | 9/2014 | Ishii | ...................... | A61B 6/4291 378/62 |
| 8,989,353 B2 * | 3/2015 | Kaneko | .................... | G21K 1/02 378/154 |
| 9,001,969 B2 * | 4/2015 | Murakoshi | ........... | A61B 6/4233 378/87 |
| 9,025,726 B2 * | 5/2015 | Ishii | .................. | G01N 23/20075 378/62 |
| 9,348,067 B2 * | 5/2016 | Vogtmeier | ........... | G02B 5/1857 |
| 9,372,269 B2 * | 6/2016 | Ho | ........................ | G01T 1/2004 |
| 9,575,188 B2 * | 2/2017 | Nitta | ...................... | B32B 38/10 |
| 9,719,947 B2 * | 8/2017 | Yun | .................. | G01N 23/20075 |
| 9,874,531 B2 * | 1/2018 | Yun | ........................ | H01J 35/08 |
| 9,899,113 B2 * | 2/2018 | Nitta | ...................... | G01T 1/2008 |
| 10,061,035 B2 * | 8/2018 | Kurebayashi | ..... | H01L 27/14663 |
| 10,256,001 B2 * | 4/2019 | Yokoyama | ............... | C25D 7/12 |
| 10,349,908 B2 * | 7/2019 | Yun | ........................ | A61B 6/508 |
| 10,393,888 B2 * | 8/2019 | Shindou | ............... | G01T 1/20 |
| 10,401,508 B2 * | 9/2019 | Sahlholm | ............... | G01T 1/202 |

(56) References Cited

U.S. PATENT DOCUMENTS

| | | | |
|---|---|---|---|
| 10,679,762 B2* | 6/2020 | Koehler | G01N 23/041 |
| 10,761,220 B2* | 9/2020 | Arimoto | G01T 1/202 |
| 10,775,518 B2* | 9/2020 | Arimoto | G01T 1/20 |
| 2003/0026386 A1 | 2/2003 | Tang | |
| 2004/0042585 A1 | 3/2004 | Nagarkar | |
| 2007/0183584 A1 | 8/2007 | Baumann | |
| 2010/0091947 A1 | 4/2010 | Niu | |
| 2012/0057677 A1 | 3/2012 | Vogtmeier | |

* cited by examiner

X-RAY DETECTOR FOR GRATING-BASED PHASE-CONTRAST IMAGING

FIELD OF THE INVENTION

The invention generally relates to grating-based phase contrast imaging. Particularly the invention relates to an X-ray detector for a phase contrast imaging system, to the use of such X-ray detector in a phase contrast imaging system, to a phase contrast imaging system with such X-ray detector and to a method of fabricating an X-ray detector for a phase contrast imaging system.

BACKGROUND OF THE INVENTION

In X-ray phase-contrast imaging and/or differential phase contrast imaging (DPCI) a phase information of coherent X-rays passing through an object of interest is visualized. In contrast to classical X-ray transmission imaging approaches, in DPCI not only absorption properties of the object of interest along a projection line, but also a phase shift of the X-rays transmitted through the object of interest and/or the small angle scattering properties of the object are determined. This provides additional information, which may be used e.g. for contrast enhancement, material composition determination, revealing of micro-structures and/or dose reduction.

Usually highly monochromatic and coherent X-ray radiation may be required in DPCI. For this purpose, conventional X-ray sources, such as e.g. X-ray tubes, may be used in combination with a source grating placed between the X-ray source and the object of interest. The source grating may ensure coherence by providing small openings, through which the X-ray beam is passed. In beam direction behind the object of interest, usually a phase-shifting grating, also known as phase grating (G1), is placed having the function of a "beam splitter". When the X-ray beam passes through the phase grating, an interference pattern is generated, which contains the required information about the phase shift of the X-ray beam in a relative position of minima and maxima of beam intensity, wherein the relative position of minima and maxima is typically in the order of several micrometers. Since a common X-ray detector with a typical resolution in the order of 150 µm may not be able to resolve such fine structures, the interference pattern usually is sampled with a phase-analyzer grating, also known as absorber grating (G2), which features a periodic pattern of transmitting and absorbing strips with a periodicity similar to and/or matching that of the interference pattern. Due to the similar periodicity of the absorber grating, a Moiré pattern is generated behind the absorber grating, which may have a much larger periodicity and which may, thus, be detectable with a conventional X-ray detector.

To finally obtain the differential phase shift, at least one of the gratings may be shifted laterally by fractions of a grating pitch, which is typically in the order of 1 µm. This technique is also referred to as "phase stepping". The phase shift can then be extracted from the particular Moiré pattern measured for each position of the analyzer grating.

In further developments, computed tomography of phase-shift with hard X-rays may also be performed. However, in particular in the case of a cone-beam geometry, rather strong phase contrast distortions may arise in regions outside a center of the field of view.

SUMMARY OF THE INVENTION

It may be desirable to provide a robust and cost-efficient X-ray detector for a phase contrast imaging system and a phase contrast imaging with such X-ray detector producing improved images with reduced phase contrast distortions.

This is achieved by the subject-matter of the independent claims, wherein further embodiments are incorporated in the dependent claims and the following description.

It should be noted that the features which are in the following described for example with respect to the X-ray detector may also be part of the phase contrast imaging system, and vice versa. Furthermore, all features which are in the following described with respect to the X-ray detector and/or the imaging system correlate to respective method steps for fabricating the X-ray detector.

A first aspect of the invention relates to an X-ray detector for a phase contrast imaging system. It is to be noted that the X-ray detector may equally be used for dark-field imaging. The X-ray detector comprises a scintillation device and a photodetector with a plurality of photosensitive pixels optically coupled to the scintillation device. The X-ray detector comprises a primary axis parallel to a surface normal vector of the scintillation device, and the scintillation device comprises a wafer substrate having a plurality of grooves, which are spaced apart from each other. Each of the grooves extends to a depth along a first direction from a first side and/or a first surface of the scintillation device into the wafer substrate, wherein each of the grooves is at least partially filled with a scintillation material. Further, the first direction of at least a part of the grooves is different from the primary axis and/or the surface normal vector, such that at least a part of the grooves is tilted with respect to and/or relative to the primary axis.

According to an example, the first direction of at least a subset of the plurality of grooves and/or at least a part of the plurality of grooves is different from the primary axis and/or different from a direction of the primary axis, such that at least the subset of the plurality of grooves and/or at least a part of the plurality of grooves is tilted with respect to the primary axis. In other words, the first direction of at least some of the plurality of grooves is different from the primary axis and/or different from a direction of the primary axis, such that at least some of the plurality of grooves are tilted with respect to the primary axis.

According to a further example, an angle between the first direction of a groove arranged in a center region of the scintillation device and the primary axis is smaller than an angle between the first direction of a groove arranged in an outer region of the scintillation device and the primary axis. In other words, an angle between the first direction of at least one groove, which is arranged in a center region of the scintillation device, and the primary axis is smaller than an angle between the first direction of at least one further groove, which is arranged in an outer region of the scintillation device, and the primary axis.

The "scintillation device" may refer to a scintillator and/or a scintillator arrangement. The primary axis may refer to an axis of the X-ray detector which may be arranged in a direction towards an X-ray source, when the X-ray detector is installed in the phase contrast imaging system. Additionally or alternatively the primary axis may be parallel to an optical axis of the imaging system and/or parallel to a center axis of an X-ray beam. In this regard, the primary axis may also refer to a beam direction along the optical axis of the imaging system. The surface normal vector may refer to the surface normal vector of the first side of the scintillation device. Alternatively, the surface normal vector may refer to the surface normal vector of a second side of the scintillation device arranged opposite to the first side. The first side may be directed towards the photodetector, whereas the second side may be directed towards an X-ray source when the X-ray detector is installed in an imaging system.

The scintillation device may have an arrangement of grooves. The grooves may also refer to trenches. Each of the grooves may have a specific first direction and/or groove direction, in which the respective groove extends from the first side of the scintillation device into the wafer substrate. Accordingly, the first direction of each of the grooves may be substantially parallel to a center axis and/or a center plane of the respective groove. By way of example, the first direction of each of the grooves may be defined by the center axis and/or the center plane of the respective groove. Each of the grooves may have a certain depth along the first direction, and each groove may be formed as elongated cavity in the wafer substrate extending along an extension direction of each groove, wherein the extension direction may be perpendicular to the surface normal vector and/or transverse to the first direction. Accordingly, each of the grooves may partly or entirely traverse the wafer substrate in the longitudinal extension direction. Further, each of the grooves may have an angle between the primary axis and the first direction of the respective groove, wherein in the following the angle may also be measured between the surface normal vector and the first direction of each groove.

By forming at least a part of the grooves such that they are tilted relative to the primary axis and/or the surface normal vector, phase contrast distortions may advantageously be reduced. This way, e.g. in a cone-beam geometry, intensity losses may be reduced by increasing an effective aspect ratio of the grooves. Thereby, the phase shift and/or dark field signal may be detected more reliably and precisely. Hence, an overall image quality may be increased.

The present invention may at least partly be regarded as being based on the following considerations and findings. Generally, grating-based differential phase contrast and/or dark-field imaging is a promising technology that may likely add additional diagnostic value in particular in the area of chest imaging, where the dark-field signal channel is highly sensitive to changes of a micro-structure of lung tissue. One of the most challenging problems related to this technology may be the fabrication of large area gratings, in particular the absorber grating G2, which is usually placed directly in front of the X-ray detector. Currently, this grating usually is a gold-grating. However, there may be a need to avoid usage of a gold grating for the G2 grating because gold has a rather weak attenuation in the medically important energy range, e.g. ranging from about 65 keV to about 82 keV. As a consequence, the G2 grating may have a rather large thickness and/or length and thus it may be rather expensive.

By using the inventive X-ray detector with its scintillation device, in which a scintillator structure is provided by at least partly filling the grooves of the wafer substrate with the scintillation material, the absorber grating may be omitted, because the functionality of the absorber grating may be provided by the X-ray detector itself and/or the scintillation device. This may save cost for the X-ray detector and/or the imaging system. By means of the inventive X-ray detector and/or the scintillation device, only a desired part of X-ray radiation may be detected, such as a part of the interference pattern generated by a phase grating (G1), which contains relevant phase shift information.

According to an embodiment of the invention, grooves arranged in the outer region of the scintillation device are more tilted with respect to the primary axis than grooves arranged in the center region of the scintillation device.

According to an embodiment of the invention, the first side of the scintillation device is in direct contact with the photodetector. This way light emitted from the grooves and/or the scintillation material contained therein may be directly transmitted to the photosensitive pixels of the X-ray detector without any absorbing materials in between. This may increase the overall efficiency of the detector.

According to an embodiment of the invention, an angle between the first direction of a groove arranged in a center region of the scintillation device and the primary axis is smaller than an angle between the first direction of a groove arranged in an outer region of the scintillation device. The X-ray detector may have a center region and/or area as well as a border region and/or area. The center region may e.g. be arranged at or adjacent to the optical axis of the imaging system, when the X-ray detector is installed therein, and the outer region may refer to a peripheral region and/or a border region of the detector, which may be arranged at a certain distance to the optical axis. i.e. it may be laterally spaced apart from the optical axis. The angles between the first directions of grooves arranged in the center region and the primary axis may be smaller than the angles of the first directions of the grooves arranged in the outer region, such that the grooves in the center region may be less tilted with respect to the primary axis than the grooves in the outer region. E.g. in a cone-beam geometry the beam may have a certain spread, such that X-ray particles impinge in different directions onto the X-ray detector with respect to the surface normal vector and/or the primary axis of the detector. By tilting the grooves arranged in the outer region more than those arranged in the center region, different impinging angles of the X-ray particles and/or the beam spread may be compensated and intensity losses may thus be reduced.

According to an embodiment of the invention, the scintillation device comprises at least one groove with a first direction parallel to the primary axis, wherein the at least one groove is arranged in a center region of the scintillation device. The at least one groove may be arranged in a center of the scintillation device and may be aligned with the primary axis and/or the optical axis of the imaging system. Alternatively or additionally a plurality of grooves arranged in the center region may have first directions parallel to each other and/or parallel to the primary axis.

According to an embodiment of the invention, an angle between the first directions of the grooves and the primary axis increases with increasing distance of the grooves to a center region of the scintillation device. The distance to the center region may be measured laterally, i.e. perpendicular and/or transverse to the primary axis, the surface normal vector and/or the optical axis. In other words, with increasing distance to the center region the grooves are sequentially more tilted and/or increasingly tilted with respect to the primary axis. This may allow to align and/or orient at least a part of the grooves or all of the grooves in direction of an X-ray source, in direction of a focal spot of the imaging system and/or in direction of a predetermined beam direction. This way, the overall intensity of X-ray radiation detected with the detector may be increased. Also an effective aspect ratio may be increased, thereby improving an overall image quality of an image acquired with the X-ray detector.

According to an embodiment of the invention, each of the grooves is completely filled with scintillation material. This may further increase an overall light output of the grooves filled with scintillation material, thereby increasing the overall detector efficiency.

According to an embodiment of the invention, each groove and/or the scintillation material contained therein is divided into a plurality of sections along a longitudinal extension direction of each groove. In other words, the scintillation material in each groove may be structured. This structure may be formed by one or more barriers ranging from the first side of the scintillation device to the depth of each groove into an inner volume of each groove and/or into the wafer substrate, wherein the barriers may separate adjacently arranged and/or directly adjoining sections. The barriers may be configured to block light generated by the scintillation material contained in a single section. Thus, light emitted in a single section may be confined within this section.

According to an embodiment of the invention, each of the grooves extends from the first side of the scintillation device into an inner volume of the wafer substrate. Alternatively or additionally the scintillation device further comprises a layer of wafer substrate arranged on a second side of the scintillation device opposite to the first side of the scintillation device. In other words, the groove may not continuously traverse the wafer substrate in the first direction, but may rather extend to a certain depth into the wafer substrate. This generally may simplify a fabrication process of the X-ray detector.

According to an embodiment of the invention, at least a part of the grooves has a rectangular, a trapezoidal, a tubular, a cylindrical, a conical, or an asymmetric shape. Accordingly, also a cross section of at least a part of the grooves may be rectangular, round, elliptic or oval. Depending on a beam geometry, certain geometries of the grooves may have certain advantages, such as trapezoid grooves in a focused geometry.

According to an embodiment of the invention, the detector is a flat detector. Alternatively or additionally, the detector is configured for a focused geometry of the imaging system. Usually, in a focused geometry, the detectors and/or gratings may be bended in order to compensate a reduction in detected X-ray intensity in peripheral and/or outer regions of the detector. With the inventive X-ray detector such bending may not be required and a manufacturing process of the X-ray detector may be simplified.

According to an embodiment of the invention, the wafer substrate comprises Silicon. Silicon may advantageously be used as rather large and homogenous wafer substrates may be available at low cost. Alternatively or additionally the scintillation material comprises at least one of CsI, NaI, CsI(Tl), CsI(Na), CsI(pure), CsF, KI(Tl), LiI(Eu) and gadolinium oxysulfide. Also other inorganic crystals may be used as scintillation material. These materials may have a rather high light output and are available at low cost.

According to an embodiment of the invention, each of the grooves has a depth of 0.5 mm to 5 mm, particularly 1 mm to 3 mm. The depth may be measured along the first direction of each groove. Alternatively or additionally, each of the grooves has a width of 1 μm to 200 μm, particularly 2 μm to 100 μm. The width may be measured perpendicular and/or transverse to the first direction of the respective groove. The above mentioned dimensions of the grooves may be suitable for differential phase contrast imaging applications, particularly for efficiently detecting the interference pattern generated by a phase grating. In this regard, the dimensions of the grooves may be similar to, balanced with and/or correlated with a periodicity of the phase grating (G1) and/or the corresponding interference pattern generated by means of the phase grating.

By way of example, an aspect ratio of the grooves and/or of each of the grooves may be in the range of 5 to 1000, particularly in the range of about 10 to 100. Therein, the aspect ratio may depend on the type and/or energy of radiation, e.g. X-rays, to be detected. Accordingly, the grooves should have a depth large enough to absorb enough radiation and/or X-ray photons. For CT applications, a stopping power of about 3 mm and for mammography applications a stopping power of about 1 mm may be suitable. Accordingly, the depth of each of the grooves may also be in this range. On the other hand, the width of the grooves may depend on the design of the phase contrast imaging system. A pitch of the grooves, a groove spacing and/or distance between two neighboring grooves may be about 1 μm to about 500 μm, particularly about 2 μm to about 100 μm, wherein a wall thickness of walls formed by the wafer substrate and separating two neighboring grooves may be about half of the pitch.

According to an embodiment of the invention, each of the grooves has a length along a longitudinal extension direction of each groove, which length corresponds to a length of a single photosensitive pixel of the photodetector. The length may be measured in a direction perpendicular and/or transverse to the first direction of each groove. In other words, the wafer substrate and/or the scintillation device may be formed such that a single groove may be covered by a single photosensitive pixel. A typical length of a photosensitive pixel may be about 100 μm to about 300 μm. Accordingly, also the length of the grooves in longitudinal extension direction may be about 100 μm to about 300 μm. A second aspect of the invention relates to the use of an X-ray detector in a phase contrast imaging system, as described above and in the following. The imaging system may e.g. refer to an imaging system with focused geometry and/or with a cone-beam geometry. The imaging system may also refer to a computed tomography system and/or a C-arm system.

A third aspect of the invention relates to a phase contrast imaging system comprising an X-ray source for emitting a beam of X-rays centered around an optical axis of the imaging system, an X-ray detector, as described above and in the following, and at least one grating arranged between the X-ray source and the X-ray detector. The optical axis may e.g. refer to a center axis and/or an axis of symmetry of the X-ray beam. The optical axis may point directly to the X-ray detector parallel to the primary axis and/or parallel to a surface normal vector of the detector. The imaging system may also comprise two gratings, wherein a first grating may be arranged between the X-ray source and the object of interest to be examined. The first grating may provide a coherent X-ray beam and/or the first grating may divide a large focal spot into several smaller ones each, wherein each of the smaller focal spots may have a spatial coherence and/or coherence length large enough to generate an interference pattern. Further, a second grating may be arranged between the object of interest and the X-ray detector, wherein the second grating may be the phase grating, which is configured for generating an interference pattern. Further, the primary axis of the X-ray detector is arranged parallel to the optical axis of the imaging system.

According to an embodiment of the invention, the X-ray detector is arranged such that the first direction of each of the grooves is oriented and/or aligned towards a focal spot of the imaging system and/or the X-ray source. The X-ray source may be a point source and the focal spot may thus refer to the location of the X-ray source. By aligning all grooves towards the focal spot, an overall detected intensity may be further increased.

A fourth aspect of the invention relates to a method of fabricating and/or manufacturing an X-ray detector. The method comprises the steps of:

forming a plurality of grooves into a wafer substrate, such that the grooves are spaced apart from each other and such that each of the grooves extends to a depth along a first direction from a surface of the wafer substrate into the wafer substrate;

at least partially filling each of the grooves with scintillation material; and arranging the wafer substrate with the at least partially filled grooves on a photodetector.

Therein, the X-ray detector comprises a primary axis parallel to a surface normal vector of the wafer substrate, and the first direction of at least a part of the grooves is different from the primary axis, such that at least a part of the grooves is tilted with respect to the primary axis.

According to an example of the fourth aspect, the first direction of at least a subset of the plurality of grooves and/or at least a part of the plurality of grooves is different from the primary axis and/or different from a direction of the primary axis, such that at least the subset of the plurality of grooves and/or at least a part of the plurality of grooves is tilted with respect to the primary axis. In other words, the first direction of at least some of the plurality of grooves is different from the primary axis and/or different from a direction of the primary axis, such that at least some of the plurality of grooves are tilted with respect to the primary axis.

According to a further example of the fourth aspect, an angle between the first direction of a groove arranged in a center region of the scintillation device and the primary axis is smaller than an angle between the first direction of a groove arranged in an outer region of the scintillation device and the primary axis. In other words, an angle between the first direction of at least one groove, which is arranged in a center region of the scintillation device, and the primary axis is smaller than an angle between the first direction of at least one further groove, which is arranged in an outer region of the scintillation device, and the primary axis.

These and other aspects of the invention will be apparent from and elucidated with reference to the embodiments described hereinafter.

BRIEF DESCRIPTION OF THE DRAWINGS

The subject matter of the invention will be explained in more detail in the following with reference to exemplary embodiments which are illustrated in the attached figures, wherein.

In principle, identical, similar and/or functionally similar parts are provided with the same reference symbols in the figures. The figures are schematically and not to scale.

DETAILED DESCRIPTION OF EMBODIMENTS

Figure 1:
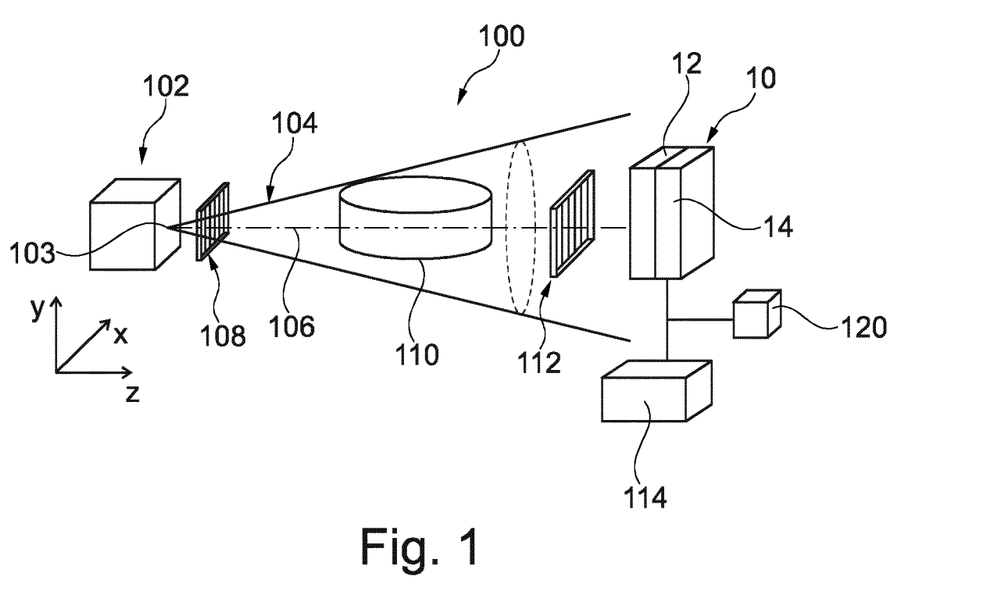
FIG. 1 shows a phase contrast imaging system according to an exemplary embodiment of the invention.

FIG. 1 shows a phase contrast imaging system 100 according to an exemplary embodiment of the invention.

The phase contrast imaging system 100 may e.g. be used for differential phase contrast imaging.

The phase contrast imaging system 100 comprises an X-ray source 102 for emitting a beam 104 of X-rays, X-ray radiation and/or X-ray photons. The X-ray source 102 may be an X-ray tube and/or a point source. The phase contrast imaging system 100 further comprises a focal spot 103. The X-ray beam 104 may be cone-like shaped and/or may be centered around an optical axis 106 of the phase contrast imaging system 100. The optical axis 106 may denote the direction of the smallest distance to the X-ray source 102 measured from a plane perpendicular to the optical axis 106. The X-ray beam 104 may be emitted in z-direction as depicted in FIG. 1.

In order to provide spatial coherence of the beam 104 and/or in order to generate a spatially coherent beam 104 of X-rays, the phase contrast imaging system 100 further comprises a source grating 108 arranged between the X-ray source 102 and an object of interest 110, which is placed inside the beam 104 and which is to be examined by means of the phase contrast imaging system 100. The source grating 108 may be a one-dimensional grid with a plurality of parallel strips. The object of interest 110 may e.g. be a patient, a part of a patient and/or any other object. Spatial coherence of the beam 104 may alternatively be provided by means of special type of X-ray source 102, such that no source grating 108 may be required.

The phase contrast imaging system 100 further comprises a phase grating 112 and an X-ray detector 10. The phase grating 112, also referred to as phase-shifting and/or G1 grating, is arranged between the object of interest 110 and the X-ray detector 10 and/or between the X-ray source 102 and the object 110. The phase grating 112 may be a one-dimensional grid with a plurality of parallel strips. The X-ray detector 10 comprises a scintillation device 12 and a photodetector 14 with a plurality of photosensitive pixels, as described in detail in following figures.

Generally, the phase grating 112 is configured to generate an interference pattern, which contains information about the phase shift of the X-ray beam 104 in a relative position of minima and maxima of beam intensity. In other words, the relative position of minima and maxima depends on the phase-shift of a wave front incident on the phase grating 112. As a phase of X-rays passing through the object of interest 110 may be altered according to physical properties of the object of interest 110, such as e.g. a density and/or a thickness of material contained therein, the interference pattern generated by the phase grating 112 is also altered accordingly. Therefore, by analyzing the interference pattern, the phase-shift information may be extracted, which information may in turn be used e.g. to increase and/or improve the contrast of an X-ray absorption image. In conventional phase contrast imaging systems the interference pattern generated by the phase grating 112 is analyzed by means of an analyzer grating (G2 grating) arranged and/or placed in front of the X-ray detector 10. In the phase contrast imaging system 100 according to the invention the functionality of the analyzer grating is advantageously integrated into the X-ray detector 10, as explained in detail in the following figures.

The phase contrast imaging system 100 further comprises a control unit, control module, controller and/or control circuitry 114 configured for controlling the X-ray detector 10, the X-ray source 102 and/or other components of the phase contrast imaging system 100. The control unit 114 may also be configured signal processing, for data read-out from the X-ray detector 10 and/or for data processing of data acquired by means of the X-ray detector 10.

The phase contrast imaging system 100 optionally comprises an actuator 120, a piezo actuator 120, a stepper 120 and/or a stepping motor 120 configured to shift the phase grating 112 and/or the X-ray detector 10 and/or the source grating 108 laterally, i.e. perpendicular and/or transverse to the optical axis 106. This may allow to obtain the differential phase shift and is also referred to as "phase stepping". The actual phase shift can then be extracted from the particular measurements for each position.

Figure 2A:
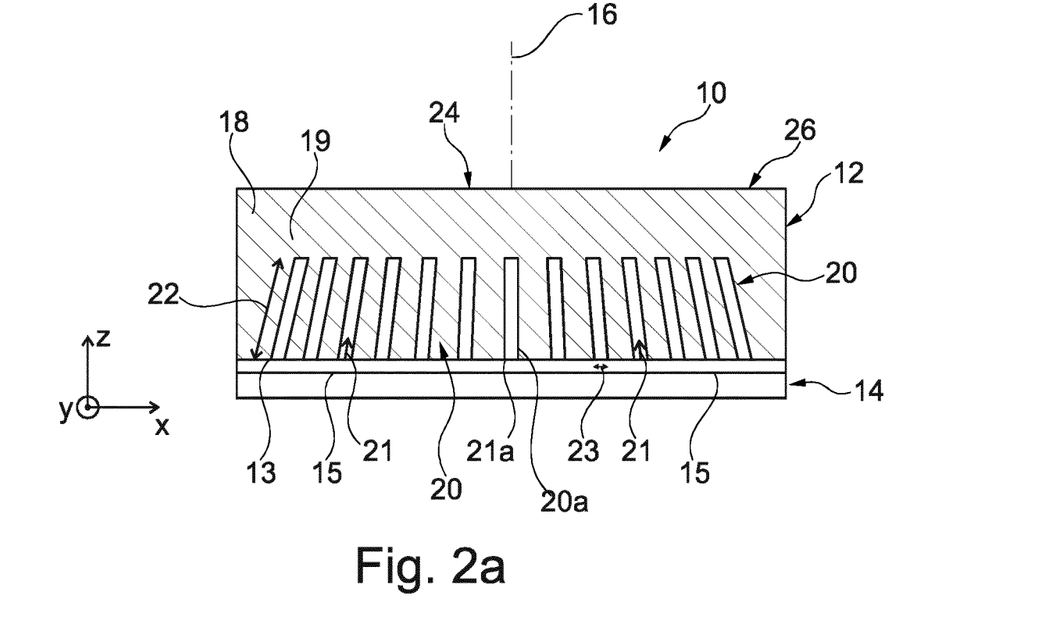
FIG. 2a shows a cross-sectional view of an X-ray detector according to an exemplary embodiment of the invention.
Figure 2B:
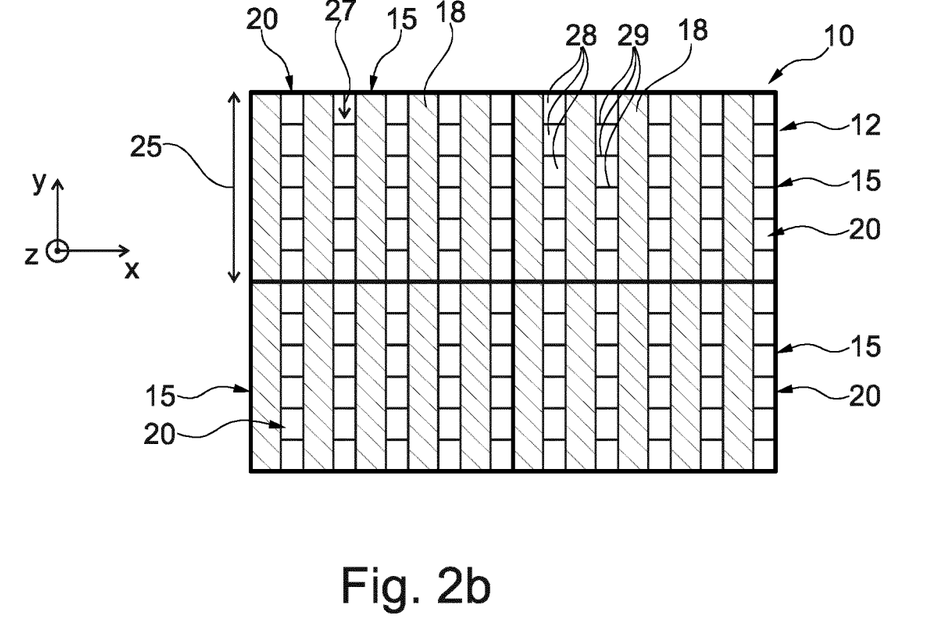
FIG. 2b shows a bottom view of an X-ray detector according to an exemplary embodiment of the invention.

FIG. 2a shows cross-sectional view of an X-ray detector 10 for a phase contrast imaging system 100 according to an exemplary embodiment of the invention. FIG. 2b shows a bottom view of an X-ray detector 10 for a phase contrast imaging system 100 according to an exemplary embodiment of the invention. If not stated otherwise, the X-ray detectors 10 of FIGS. 2a and 2b comprise the same elements and features as the X-ray detector 10 of FIG. 1.

The X-ray detector 10 is a flat X-ray detector 10, which comprises a scintillation device 12 and a photodetector 14 with photosensitive pixels 15 optically coupled to the scintillation device 12. The photosensitive pixels 15 are schematically depicted in FIG. 2b as rectangles 15. The X-ray detector 10 has a primary axis 16, which is oriented and/or aligned parallel to a surface normal vector of the X-ray detector 10 and/or parallel to a surface normal vector of the scintillation device 12. The primary axis 16 may be aligned with the optical axis 106 of the phase-contrast imaging system 100, i.e. the primary axis 16 may be directed towards the focal spot 103 and/or towards the X-ray source 102, when the X-ray detector 10 is installed in the phase-contrast imaging system 100. The surface normal vector may denote a vector of a first side 13 and/or a first surface 13 of the scintillation device 12. However, the surface normal vector may also denote the respective vector on a further side/surface of the scintillation device opposite to the first side 13.

The scintillation device 12 comprises a silicon wafer substrate 18, e.g. a silicon wafer substrate, having grooves 20 and/car trenches 20, which are spaced apart from each other in a direction perpendicular and/or transverse to the primary axis 16. As shown in FIGS. 2a and 2b, the grooves 20 are spaced apart from each other in x-direction, wherein between two neighboring grooves 20, the wafer substrate 18 is arranged. The grooves 20 may be equally spaced apart from each other in x-direction and/or they may be arranged with varying distance between two neighboring grooves 20. The grooves 20 thereby are spaced apart from each other by the wafer substrate 18. Each of the grooves 20 extends to a depth 22 along a first direction 21 from the first side 13 of the scintillation device 12 into an inner volume 19 of the wafer substrate 18. The first direction 21 is schematically depicted in FIG. 2a by an arrow 21 for two of the grooves 20. Accordingly, each of the grooves 20 has a specific first direction 21 and/or a specific depth 22, which may refer to groove direction 21 of each groove 20.

The first directions 21 of at least a part of the grooves 20 are different from the primary axis 16 and/or the surface normal vector of the X-ray detector 10, such that at least a part of the grooves 20 is tilted with respect to the primary axis 16. In other words, the first directions 21 of at least a part of the grooves 20 are oriented transverse to the surface normal vector of the X-ray detector 10 and/or with a transverse component to the surface normal vector of the X-ray detector 10.

Particularly, angles between the first directions 21 of grooves 20, which are arranged in a center and/or middle region 24 of the scintillation device 12, and the primary axis 16 are smaller than angles between the first directions 21 of grooves 20, which are arranged in an outer region 26 and/or peripheral region 26 of the scintillation device 12. Accordingly, grooves 20 arranged in the outer region 26 are more tilted with respect to the primary axis 16 than grooves 20 arranged in the center region 24.

Further, at least one groove 20a arranged in the center region 24 has a first direction 21a parallel to the primary axis 16 and/or the surface normal vector of the detector 10. Also a plurality of grooves 20 in the center region 24 may have first directions 21a parallel to the primary axis 16 and/or the surface normal vector of the detector 10.

Further, the grooves 20 may be formed in the wafer substrate 18, such that the angles between the first directions 21 of the grooves 20 and the primary axis 16 increase with increasing distance of the grooves 20 to the center region 24 of the scintillation device 12. In other words, the greater the distance of a groove 20 to the center region 24 and/or to a center of the scintillation device 12 is, the more is the respective groove 20 tilted with respect to the primary axis 16. Accordingly, the grooves 20 are increasingly tilted with increasing distance to the center region 24.

Each of the grooves 20 has a depth 22 of about 0.5 mm to about 5 mm, particularly about 1 mm to about 3 mm, measured along the first direction 21. Further, each of the grooves 20 has a width_23 of about 1 μm to about 200 μm, particularly about 2 μm to about 100 μm, measured perpendicular to the primary axis 16 in x-direction as shown in FIG. 2a.

Referring to FIG. 2b, each of the grooves 20 has length 25 along a longitudinal extension direction 27, wherein the length 25 corresponds and/or correlates with the length of a single photosensitive pixel 15. A typical length 25 of the grooves 20 may be in the range of about 100 μm to about 300 μm. The extension direction 27 of each groove 20 is oriented antiparallel to the y-axis in FIG. 2b. Each of the grooves 20 may entirely traverse the wafer substrate 18 along the longitudinal extension direction 27, i.e. in the example shown in FIG. 2b the length of a single groove 20 may be twice as large as the length of a photosensitive pixel 15. Alternatively, a single groove 20 may have a length 25 nearly equal to the length of the photosensitive pixel 15, i.e. in y-direction as shown in FIG. 2b two grooves 20 may be arranged, adjoining each other in y-direction and/or in the longitudinal extension direction 27. Further, as can be seen in FIG. 2b the extension directions 27 of the grooves 20 are parallel with respect to each other, and the grooves 20 are separated by the wafer substrate 18 in a direction perpendicular to the extension direction 27, i.e. in x-direction.

Each of the grooves 20 is at least partly, preferably completely, filled with scintillation material. The scintillation material may comprise at least one of CsI, NaI, CsI(Tl), CsI(Na), CsI(pure), CsF, KI(Tl), LiI(Eu) and gadolinium oxysulfide. Also other crystals may be used as scintillation material.

X-ray photons emitted from the X-ray source 102 and passing through the source grating 108, the object of interest 110 and/or the phase grating 112 impinge onto the X-ray detector 10 and the grooves 20. Inside the grooves 20, X-ray photons are converted to visible light, which in turn is converted to an electrical signal by means of the photosensitive pixels 15. Finally, the electrical signal may be processed and/or evaluated by the control unit 114. Since light generated by an impinging X-ray photon in the scintillation material of the scintillator device 12 is emitted in all directions, each groove 20 and/or the scintillation material comprised in each groove 20 is divided into several sections 28 along the longitudinal extension direction 27. In other words, the scintillation material in each groove 20 is structured. The sections 28 may be provided by forming appropriate barriers 29 in the scintillation material of each groove 20. The barriers 29 may extend from the first side 13 of the scintillation device 12 to the depth 22 of each groove 20. By means of the sections 28 and/or barriers 29 it may be ensured that light generated by an X-ray photon in a single section 28 is collimated and/or refined within the respective section 28. Accordingly, light generated in a specific section 28 may not cross a barrier 29. This may also increase a resolution of the X-ray detector 10. The section 28 may extend in extension direction 27 to be as large as an area covered by a single photosensitive pixel 15 in the extension direction 27. In other words, the section 28 and a single photosensitive pixel 16 may have identical extensions and/or dimensions in extension direction 27.

Referring to FIG. 2a, a cross-sectional shape of the grooves 20 may be trapezoidal. However, other shapes, such as a rectangular, a tubular, a cylindrical, a conical, or an asymmetric shape may be feasible depending e.g. on beam geometry.

It is to be noted that also a two-dimensional grid with grooves 20 may be fabricated and/or used for the X-ray detector 10. Accordingly, the grooves 20 may be arranged in a pattern, a two-dimensional grid and/or an array in the wafer substrate 18. This may allow to extract two-dimensional phase-shift information with the X-ray detector 10.

Figure 3:
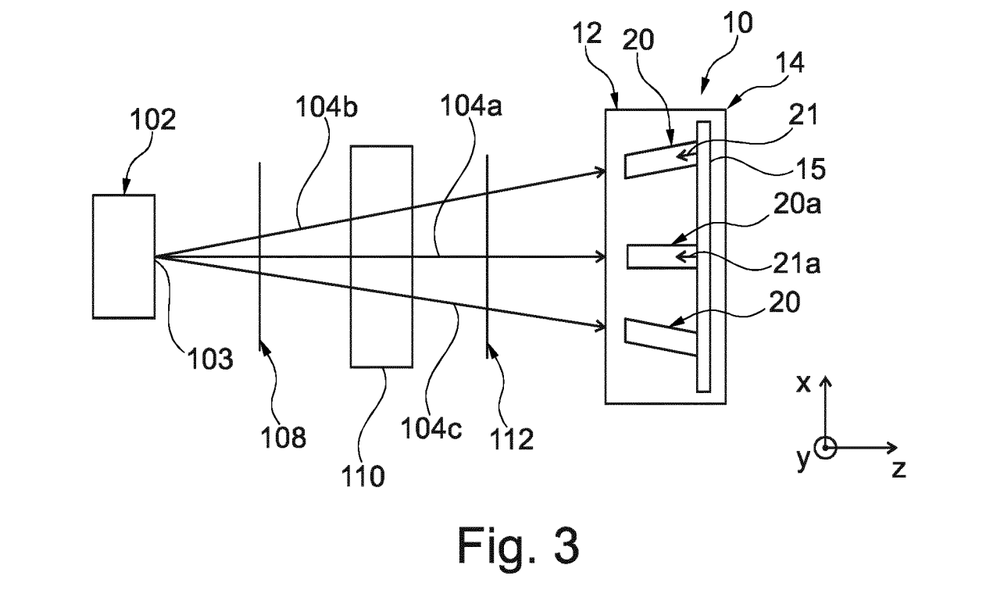
FIG. 3 shows a cross-sectional view of a phase contrast imaging system according to an exemplary embodiment of the invention.

FIG. 3 shows a cross-sectional view of a phase contrast imaging system 100 according to an exemplary embodiment of the invention. If not stated otherwise, the imaging system 100 of FIG. 3 comprises the same elements and features as the imaging system 100 of FIG. 1 and/or the X-ray detector 10 as described with reference to FIGS. 2a and 2b.

For the sake of visibility, the X-ray detector 10 shown in FIG. 3 comprises only 3 grooves 20, 20a. However, the X-ray detector 10 may comprise many more grooves 20.

In FIG. 3, three different impinging directions 104a, 104b, 104c of an X-ray beam 104 are schematically depicted to illustrate advantages of the inventive X-ray detector 10 and/or the imaging system 100. In this focused geometry shown in FIG. 3, each of the grooves 20, 20a and/or the respective first directions 21, 21a of each of the grooves 20, 20a is oriented and/or aligned towards the focal spot 103 of the imaging system 100 and/or towards the X-ray source 102. Accordingly, the first direction 21, 21a of each groove 20, 20a is direct antiparallel to the respective impinging direction 104a, 104b, 104c of X-rays. This design advantageously allows to reduce losses in an intensity detected with the X-ray detector 10 by increasing the effective aspect ratio. Accordingly, phase contrast distortions may be reduced and an overall image quality may be improved.

Typically, a large area detector 10 may have size of about 50 cm times 50 cm, which is illuminated by the X-ray source 102 in a distance D of about 50 cm to 200 cm. This implies that the x-ray photons incident under an angle to the surface normal vector of the X-ray detector 10 and/or a respective detector plane, increases with increasing distance to the optical axis 106. Near the borders of the detector 10 and/or in the outer region 26 of the X-ray detector 10 the maximum angle α is equal to arcustangens(a/2/D)), wherein a refers to a dimension of the detector 10 in a direction perpendicular to the optical axis 16. Therefore, the visibility and also the detected intensity is reduced for the peripheral area 26 and/or outer region 26 of the detector 10. With the inventive detector 10 this problem may significantly be reduced and/or solved completely.

Figure 4:
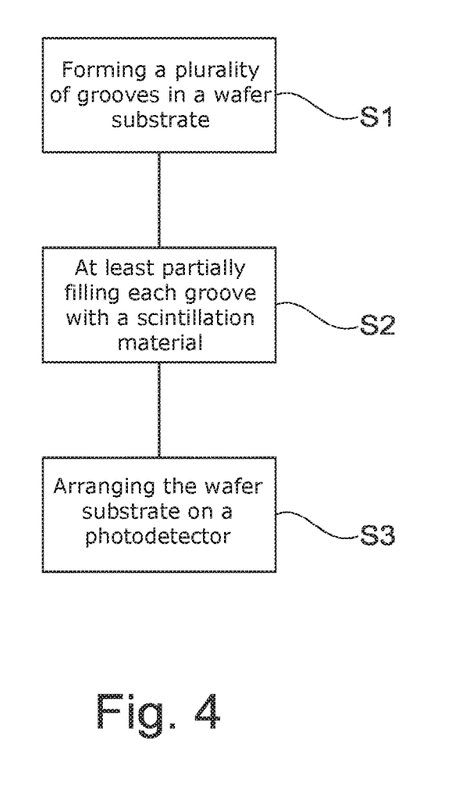
FIG. 4 shows a flow chart illustrating steps of a method of fabricating an X-ray detector according to an exemplary embodiment of the invention.

FIG. 4 shows a flow chart illustrating steps of a method of fabricating an X-ray detector 10 according to an exemplary embodiment of the invention.

In a step S1 a plurality of grooves 20 is formed into a wafer substrate 18, such that the grooves 20 are spaced apart from each other and such that each of the grooves 20 extends to a depth 22 along a first direction 21 from a surface 13 of the wafer substrate 18 and/or a first side 13 into the wafer substrate 18;

In a second step S2 each of the grooves 20 is at least partially filled with scintillation material.

In a third step S3 the wafer substrate 18 is arranged with the at least partially filled grooves 20 on a photodetector 14.

The X-ray detector 10 fabricated and/or manufactured with this method may comprise the same features and/or elements as the X-ray detectors 10 described in previous FIGS. 1 to 3.

Particularly the X-ray detector 10 comprises a primary axis 16 parallel to a surface normal vector of the wafer substrate 18, wherein the first direction 21 of at least a part of the grooves 20 is different from the primary axis 16, such that at least a part of the grooves 20 is tilted with respect to the primary axis 16.

The grooves 20 may for instance be etched and/or drilled into the wafer substrate 18 in step S1. By way of example, the grooves 20 may be formed with a laser, and optionally surfaces of the grooves 20 may be smoothed with an etching process.

In order to determine the first directions 21 of each of the grooves 20, a laser and/or an X-ray source may be used in combination with a shadow mask. This may allow to simulate impinging directions 104a, 104b, 104c of X-rays onto the X-ray detector 10 and/or simulating a beam geometry. This may allow each groove 20 and/or each first direction 21 to be aligned with the respective predetermined impinging direction 104a, 104b, 104c of X-rays, as illustrated in FIG. 3.

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art and practicing the claimed invention, from a study of the drawings, the disclosure, and the appended claims.

In the claims, the word "comprising" does not exclude other elements or steps, and the indefinite article "a" or "an" does not exclude a plurality. The mere fact that certain measures are recited in mutually different dependent claims does not indicate that a combination of these measures cannot be used to advantage. Any reference signs in the claims should not be construed as limiting the scope.

The invention claimed is:

1. An X-ray detector for phase contrast imaging, the X-ray detector comprising:
   a scintillation device comprising a wafer substrate having a plurality of grooves spaced apart from each other, wherein each groove of the plurality of grooves extends to a depth along a first direction from a first side of the scintillation device into the wafer substrate, each groove of the plurality of grooves being at least partially filled with a scintillation material; and a photodetector comprising a plurality of photosensitive pixels optically coupled to the scintillation device;
  wherein a primary axis is substantially parallel to a surface normal vector of the scintillation device;
  wherein first directions of at least a part of the plurality of grooves are different from the primary axis, such that at least a part of the plurality of grooves is tilted with respect to the primary axis; and
  wherein an angle between a first direction of a groove arranged in a center region of the scintillation device and the primary axis is smaller than an angle between a first direction of a groove arranged in an outer region of the scintillation device and the primary axis.

2. The X-ray detector according to claim 1, wherein grooves of the plurality of grooves arranged in an outer region are more tilted with respect to the primary axis than grooves of the plurality of grooves arranged in a center region.

3. The X-ray detector according to claim 1, wherein at least one groove of the plurality of grooves has a first direction parallel to the primary axis; and wherein the at least one groove of the plurality of grooves is arranged in a center region of the scintillation device.

4. The X-ray detector according to claim 1, wherein an angle between a first direction of a groove of the plurality of grooves and the primary axis increases with an increasing distance of the groove of the plurality of grooves from a center region to an outer region of the scintillation device.

5. The X-ray detector according claim 1, wherein each groove of the plurality of grooves is completely filled with a scintillation material.

6. The X-ray detector according to claim 1, wherein each groove of the plurality of grooves is divided into a plurality of sections along a longitudinal extension direction.

7. The X-ray detector according to claim 1, wherein at least a part of the plurality of grooves has at least one of the following shapes: a rectangular shape, a trapezoidal shape, a tubular shape, a cylindrical shape, a conical shape, and an asymmetric shape.

8. The X-ray detector according to claim 1, wherein the detector comprises a flat detector.

9. The X-ray detector according to claim 1, wherein the wafer substrate comprises silicone; and/or wherein the scintillation material comprises at least one of CsI, NaI, CsI(Tl), CsI(Na), CsI(pure), CsF, KI(Tl), LiI(Eu) and gadolinium oxysulfide.

10. The X-ray detector according to claim 1, wherein each groove of the plurality of grooves has a depth of about 0.5 mm to 5 mm; and/or wherein each groove of the plurality of grooves has a width of about 1 µm to 200 µm.

11. The X-ray detector according to claim 1, wherein each groove of the plurality of grooves has a length along a longitudinal extension direction that corresponds to a length of a photosensitive pixel of the plurality of photosensitive pixels.

12. A phase contrast imaging system, comprising:
  an X-ray source for emitting a beam of X-rays centered around an optical axis;
  an X-ray detector comprising:
    a scintillation device comprising a wafer substrate having a plurality of grooves spaced apart from each other, wherein each groove of the plurality of grooves extends to a depth along a first direction from a first side of the scintillation device into the wafer substrate, each groove of the plurality of grooves being at least partially filled with a scintillation material; and
    a photodetector comprising a plurality of photosensitive pixels optically coupled to the scintillation device, wherein a primary axis of the X-ray detector is substantially parallel to a surface normal vector of the scintillation device, wherein the first direction of at least a part of the plurality of grooves is different from the primary axis, such that at least a part of the plurality of grooves is tilted with respect to the primary axis, and wherein an angle between the first direction of a groove of the plurality of grooves arranged in a center region of the scintillation device and the primary axis is smaller than an angle between the first direction of a groove of the plurality of grooves arranged in an outer region of the scintillation device and the primary axis; and
  at least one grating arranged between the X-ray source and the X-ray detector, wherein the primary axis of the X-ray detector is substantially parallel to the optical axis.

13. The phase contrast imaging system according to claim 12, wherein the X-ray detector is arranged such that the first direction of each groove of the plurality of grooves is oriented towards a focal spot of the X-ray source.

14. A method of fabricating an X-ray detector, the method comprising:
  forming a plurality of grooves into a wafer substrate of a scintillation device, such that the plurality of grooves are spaced apart from each other and such that each groove of the plurality of grooves extends to a depth along a first direction from a surface of the wafer substrate into the wafer substrate;
  at least partially filling each groove of the plurality of grooves with a scintillation material; and
  arranging the wafer substrate with the at least partially filled plurality of grooves on a photodetector;
  wherein the X-ray detector comprises a primary axis parallel to a surface normal vector of the wafer substrate;
  wherein the first direction of at least a part of the plurality of grooves is different from the primary axis, such that at least a part of the plurality of grooves is tilted with respect to the primary axis, and
  wherein an angle between the first direction of a groove of the plurality of grooves arranged in a center region of the scintillation device and the primary axis is smaller than an angle between the first direction of a groove of the plurality of grooves arranged in an outer region of the scintillation device and the primary axis.

* * * * *